(12) United States Patent
Dabrowiak (10) Patent No.: US 10,869,989 B2
(45) Date of Patent: Dec. 22, 2020

(54) HEAT EXCHANGE CATHETERS AND THEIR METHODS OF MANUFACTURE AND USE

(71) Applicant: ZOLL Circulation, Inc., San Jose, CA (US)

(72) Inventor: Jeremy Thomas Dabrowiak, Santa Clara, CA (US)

(73) Assignee: Zoll Circulation, Inc., San Jose, CA (US)

( * ) Notice: Subject to any disclaimer, the term of this patent is extended or adjusted under 35 U.S.C. 154(b) by 465 days.

(21) Appl. No.: 15/350,918

(22) Filed: Nov. 14, 2016

(65) Prior Publication Data
US 2017/0182286 A1    Jun. 29, 2017

Related U.S. Application Data

(63) Continuation of application No. 13/631,410, filed on Sep. 28, 2012, now Pat. No. 9,492,633.
(Continued)

(51) Int. Cl.
*A61M 25/00* (2006.01)
*A61F 7/00* (2006.01)
(Continued)

(52) U.S. Cl.
CPC ....... *A61M 25/0026* (2013.01); *A61F 7/0085* (2013.01); *A61F 7/12* (2013.01);
(Continued)

(58) Field of Classification Search
CPC .......... A61M 25/0015; A61M 25/0026; A61M 25/0009; A61M 25/007;
(Continued)

(56) References Cited

U.S. PATENT DOCUMENTS

| 4,259,276 | A |   | 3/1981 | Rawlings |         |
|-----------|---|---|--------|----------|---------|
| 5,411,477 | A | * | 5/1995 | Saab ......................... A61F 7/123 |
|           |   |   |        |          | 264/521 |

(Continued)

FOREIGN PATENT DOCUMENTS

| JP | 2003-503123 A | 1/2003 |
| JP | 2003-507119   | 2/2003 |

(Continued)

OTHER PUBLICATIONS

Office Action dated May 22, 2018 in corresponding Japanese Patent Application No. 2017-121245.
(Continued)

*Primary Examiner* — Manuel A Mendez
*Assistant Examiner* — Justin L Zamory
(74) *Attorney, Agent, or Firm* — Fish & Richardson P.C.

(57) ABSTRACT

A closed loop catheter useable for heat exchange is manufactured by forming a plurality of generally transverse bore holes though a flexible, multilumen catheter body, lacing a tube trough the bore holes so that loops of the tube protrude from the catheter body, connecting one end of the tube to an inflow lumen of the catheter and connecting the other end of the tube to an outflow lumen of the catheter. A heated or cooled heat exchange medium may then be circulated through the tube while the catheter is inserted in the vasculature of a subject, thereby resulting in heat exchange between the subject's flowing blood and the heat exchange medium being circulated through the tube.

26 Claims, 4 Drawing Sheets

Related U.S. Application Data (60) Provisional application No. 61/542,004, filed on Sep. 30, 2011.

(51) Int. Cl.
  *A61F 7/12* (2006.01)
  *A61M 25/09* (2006.01)
  *A61F 7/02* (2006.01)
  *A61M 25/01* (2006.01)

(52) U.S. Cl.
  CPC ...... *A61M 25/007* (2013.01); *A61M 25/0015* (2013.01); *A61M 25/09* (2013.01); *A61F 2007/0054* (2013.01); *A61F 2007/0056* (2013.01); *A61F 2007/0096* (2013.01); *A61F 2007/0098* (2013.01); *A61F 2007/0261* (2013.01); *A61F 2007/126* (2013.01); *A61M 2025/0183* (2013.01); *Y10T 29/49826* (2015.01)

(58) Field of Classification Search
  CPC .. A61M 2025/0163; A61M 2205/3368; A61M 2205/36; A61M 2205/366; A61F 2007/126; A61F 2007/0085
  See application file for complete search history.

(56) References Cited

U.S. PATENT DOCUMENTS

| | | | |
|---|---|---|---|
| 5,441,516 A * | 8/1995 | Wang | A61B 17/22 604/104 |
| 6,237,355 B1 | 5/2001 | Li | |
| 6,264,679 B1 | 7/2001 | Keller et al. | |
| 6,589,271 B1 | 7/2003 | Tzeng et al. | |
| 6,592,612 B1 | 7/2003 | Samson et al. | |
| 6,673,042 B1 | 1/2004 | Samson et al. | |
| 6,749,625 B2 | 6/2004 | Pompa et al. | |
| 6,796,995 B2 | 9/2004 | Pham et al. | |
| 7,255,709 B2 | 8/2007 | Walker et al. | |
| 7,566,341 B2 | 7/2009 | Keller et al. | |
| 7,963,986 B2 | 6/2011 | Machold et al. | |
| 2002/0116039 A1 | 8/2002 | Walker et al. | |
| 2002/0183816 A1* | 12/2002 | Tzeng | A61F 7/12 607/105 |
| 2002/0193738 A1 | 12/2002 | Adzich et al. | |
| 2007/0191810 A1 | 8/2007 | Kennedy | |
| 2013/0090593 A1 | 4/2013 | Dabrowiak | |

FOREIGN PATENT DOCUMENTS

| | | |
|---|---|---|
| JP | 2003-507119 A | 2/2003 |
| JP | 2003-523806 | 8/2003 |
| JP | 2004-504110 A | 2/2004 |
| JP | 2007-501689 A | 2/2007 |
| JP | 2017-159132 | 9/2017 |
| WO | WO99/52455 A1 | 10/1999 |
| WO | WO 2001/052781 A1 | 7/2001 |

OTHER PUBLICATIONS

International Search Report and Written Opinion for corresponding PCT/US2012/058058. International filing date Sep. 28, 2012.
Supplementary European Search Report dated May 28, 2015 in related European Application No. EP12834886.9.
Office Action dated Jun. 14, 2016 in corresponding Japanese Patent Application No. 2014-533427.
European Search Report dated Apr. 18, 2017 in related European Application No. 16203898.8.
Japanese Office Action in Application No. 2019-049184, dated Feb. 7, 2020, 6 pages.

* cited by examiner

HEAT EXCHANGE CATHETERS AND THEIR METHODS OF MANUFACTURE AND USE

RELATED APPLICATION

This is a continuation of U.S. patent application Ser. No. 13/631,410 filed Sep. 28, 2012 and issuing on Nov. 15, 2016 as U.S. Pat. No. 9,492,633, which claims priority to U.S. Provisional Patent Application No. 61/542,044 filed Sep. 30, 2011, the entire disclosure of each such application being expressly incorporated herein by reference.

FIELD OF THE INVENTION

The present invention relates to medicine and biomedical engineering and more particularly to heat exchange catheter devices and their methods of manufacture and use.

BACKGROUND OF THE INVENTION

Pursuant to 37 CFR 1.71(e), this patent document contains material which is subject to copyright protection. The copyright owner has no objection to facsimile reproduction of the entire patent document or the patent disclosure, as it appears in the Patent and Trademark Office patent file or records, but otherwise reserves all copyright rights whatsoever.

Hypothermia can be induced in humans and some animals for the purpose of protecting various organs and tissues (e.g., hear, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), postanoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by endovascular temperature management (ETM) wherein a heat exchange catheter is inserted into a blood vessel and a thermal exchange fluid is then circulated through the heat exchange catheter. This technique can effectively cool blood flowing through the subject's vasculature and, as a result, lower the core body temperature of the subject to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

A number of heat exchange catheters are currently available for use in ETM. One such catheter, the Solex™ Catheter available from ZOLL Circulation, Inc. of Sunnyvale, Calif., generally comprises a flexible catheter shaft having curved loops of tubing protruding from opposite sides of a distal portion of the catheter. In operation, the distal portion of the Solex™ catheter is inserted into the vasculature of a subject and a heated or cooled thermal exchange medium is then circulated through the curved loops of tubing. This results in exchange of heat between the circulating thermal exchange medium and blood flowing through the subject's vasculature, without causing the thermal exchange medium to be infused into the subject's bloodstream.

The current Solex™ catheter is formed of two subassemblies, a proximal portion and a distal portion. The proximal portion is a dual lumen tube that has an inflow lumen through which the thermal exchange fluid flows in the distal direction and an outflow lumen through which the thermal exchange fluid flows in the proximal direction. The distal portion is a coiled shaft with thin walled tubing "sewn" onto it to form the protruding curved loops of tubing. These proximal and distal portions are then joined together to make the final catheter. This two-piece construction requires a jointure or connection midway along the catheter shaft and is relatively labor intensive.

Additionally, the coiled shaft on the distal portion of the Solex™ catheter gives rise to a "bumpy" feel as the catheter is withdrawn through a vascular introducer, such as during removal of the catheter from the subject's body. The elimination of the coiled distal shaft in favor of a smoother one-piece shaft could lessen or eliminate such "bumpy" feel as the catheter is being removed from the patient.

Accordingly, there exists a need in the art for the development of new methods for catheter manufacture that may be used for the manufacture of the Solex™ catheter and/or other catheters having similar construction, thereby eliminating the need for formation of a jointure or connection midway along the catheter shaft and potentially offering other advantages, such as; 1) reducing the number of parts used in manufacturing the catheter and/or 2) reducing the labor and manual endeavor required for manufacture of the catheter, such as eliminating the need for the delicate sewing step to attach the thin-walled tubing to the coiled shaft and/or 3) reducing or eliminating the "bumpy" feel that the catheter has when being removed from the patient.

SUMMARY OF THE INVENTIONS

In accordance with the present invention, there is provided a catheter device having a one-piece or unitary catheter shaft with protruding loops of tubing which form a closed-loop recirculation circuit through which thermal exchange fluid or other flowable matter may be circulated.

Further in accordance with the present invention, there is provided a catheter device comprising: a) an elongate catheter body having, a proximal end, a distal end, an inflow lumen and an outflow lumen; b) a plurality of bores extending transversely through the catheter body at spaced-apart locations; c) a tube having a first end connected to the inflow lumen and a second end connected to the outflow lumen, said tube passing in alternate transverse directions through adjacent ones of said bores such that tubing loops comprising portions of said tube protrude outwardly from opposite sides of the catheter body.

Still further in accordance with the present invention, there is provided a method for manufacturing a catheter device, said method comprising the steps of: a) providing or obtaining an elongate catheter body having, a proximal end, a distal end, an inflow lumen and an outflow lumen; b) forming a plurality of bores transversely through the catheter body at spaced-apart locations; c) passing a tube in alternate transverse directions through adjacent ones of said bores such that loops of the tube protrude outwardly from opposite sides of the catheter body; d) connecting a first end of the tube to the inflow lumen; and e) connecting a second end of the tube to the outflow lumen. The bores may be formed by any suitable means such as drilling, punching, laser cutting, blade cutting, water jet cutting, or other manual or automated techniques known in the art. In some embodiments, the bores may be formed by advancing a punch through the catheter body at an angle (e.g., substantially a right angle or any other desired angle) relative to a longitudinal axis of the catheter body. If oval or ovoid bores are desired, such punch may be of oval or ovoid shape.

Still further aspects and details of the present invention will be understood upon reading of the detailed description and examples set forth herebelow.

DETAILED DESCRIPTION OF THE INVENTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
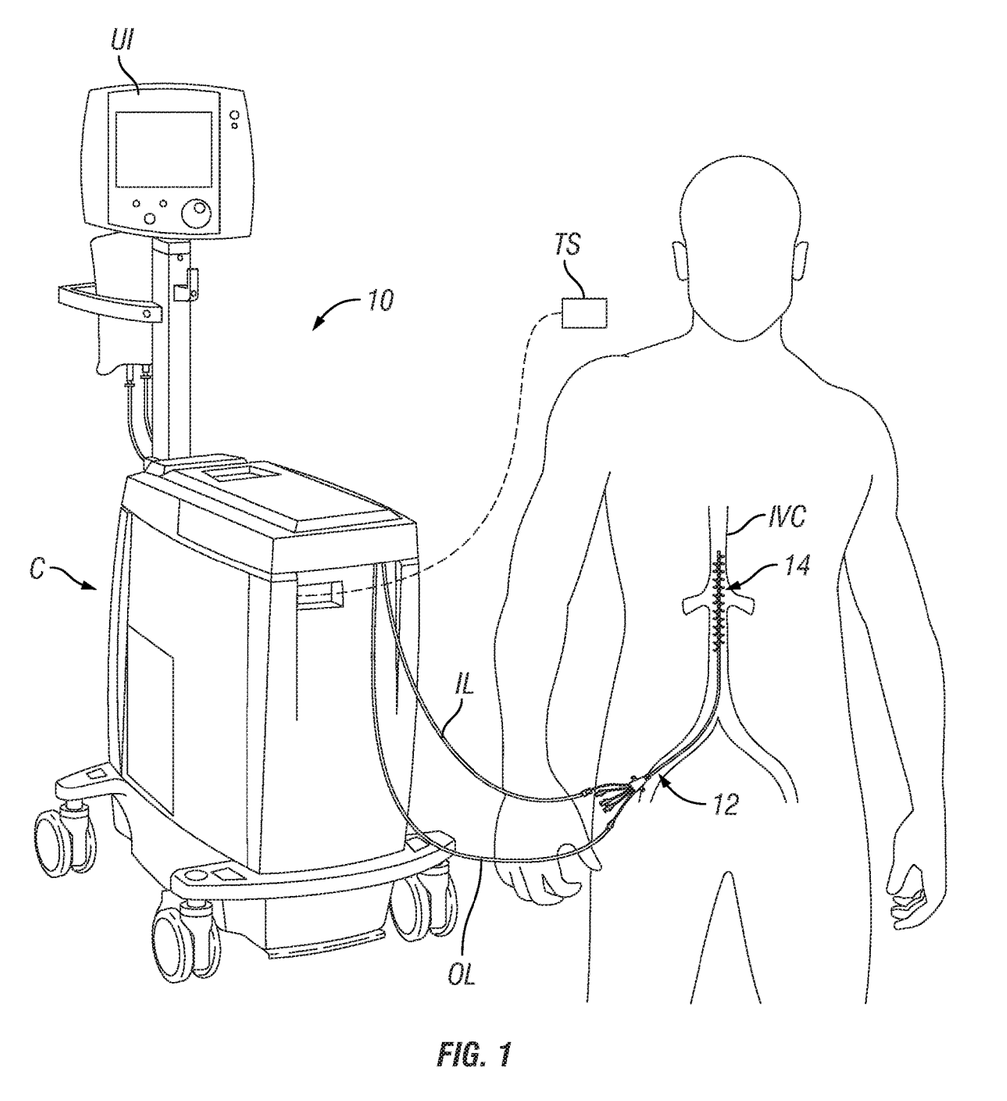
FIG. 1 is a schematic diagram of an endovascular temperature management system of the present invention.

FIG. 1 is a schematic diagram of an endovascular temperature management system 10 which comprises a heat exchange catheter 12 of a type having heat exchange tubing loops 14, an extracorporeal control console C and at least one body temperature sensor TS. In this example, the extracorporeal console C contains a controller (e.g., a microprocessor controller), a user interface UI for inputting data to the controller, a heater/cooler for adjusting the temperature of a thermal exchange medium (e.g., 0.9% sodium chloride solution) and a pump for pumping the thermal exchange medium.

The catheter 12 is connected to the extracorporeal console C by way of an inflow line IL and an outflow line OL so that the pump within the console C will circulate temperature-controlled thermal exchange medium through heat exchange tubing loops 14 which protrude from a distal portion of the heat exchange catheter 12. In operation, the catheter 12 is inserted into the vasculature of a subject so that blood flowing through the subject's vasculature will pass over and in heat exchange proximity with the heat exchange tubing loops 14, thereby allowing heat to be exchanged between the circulating thermal exchange medium and the subject's flowing blood. Warming or cooling of the subject's flowing blood then results in warming or cooling of all or a desired portion of the subject's body. In the particular non-limiting example shown in FIG. 1, the distal portion of the catheter 12 is positioned so that the heat exchange tubing loops 14 reside within the subject's inferior vena cava IVC, such catheter positioning being suitable for applications wherein whole body temperature management is desired.

The temperature sensor(s) TS may be positioned on or in the subject's body to measure the temperature of all or part of the body where it is desired to effect temperature modification or control. The controller within the console C receives signals from the temperature sensor(s) TS indicating the currently sensed body temperature. A desired target temperature may be input via the user interface UI and the controller will then issue control signals to the heater cooler and/or pump to adjust the temperature and/or the flowate of the heat exchange medium in an effort to attain and/or maintain the target body temperature. A control console of the type shown in FIG. 1 and described in this example is commercially available as the Thermogard XP™ Temperature Management System from ZOLL Circulation of Sunnyvale, Calif. Other potentially useable control consoles are available from other sources and/or described in the following United States patents and published patent applications, the entire disclosures of which are expressly incorporated herein by reference:

The catheter 12 of this example is constructed and manufactured in the manner shown in FIGS. 2-4A. A one-piece catheter body 12 is used in this example. As may be appreciated from the cross-sectional views of FIGS. 3A-3C, the catheter body 12 of this example has an inflow lumen 17, an outflow lumen 15, an optional distal infusion or guidewire lumen 16, an optional medial infusion lumen 18 and an optional proximal infusion lumen 19. The individual lumens 15, 16, 17, 18, 19 may be integrally formed (e.g., extruded) within the catheter body 12 or may comprise one or more separate tube(s) that are passed through a lumen of the catheter body 12. In this particular example, the one-piece catheter body is formed of an extruded multilumen tube. Also, in this example, the catheter body 12 has an optional atraumatic distal tip member 11 attached to its distal end.

Figure 2:
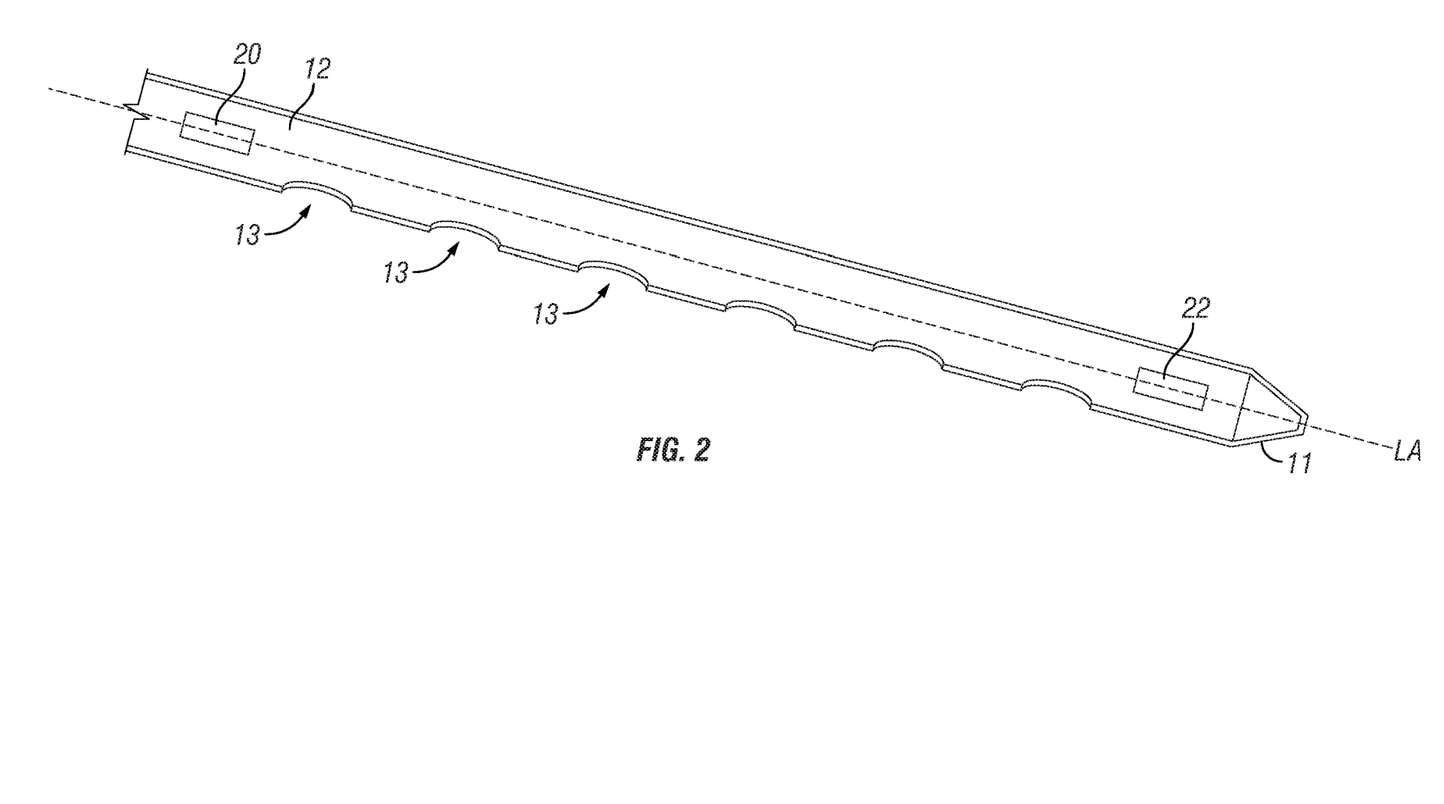
FIG. 2 is a partial perspective view of a portion of a catheter body having a plurality of transverse bores formed therein during manufacture of a catheter device of the present invention.
Figures 3, 3A, 3B, 3C:
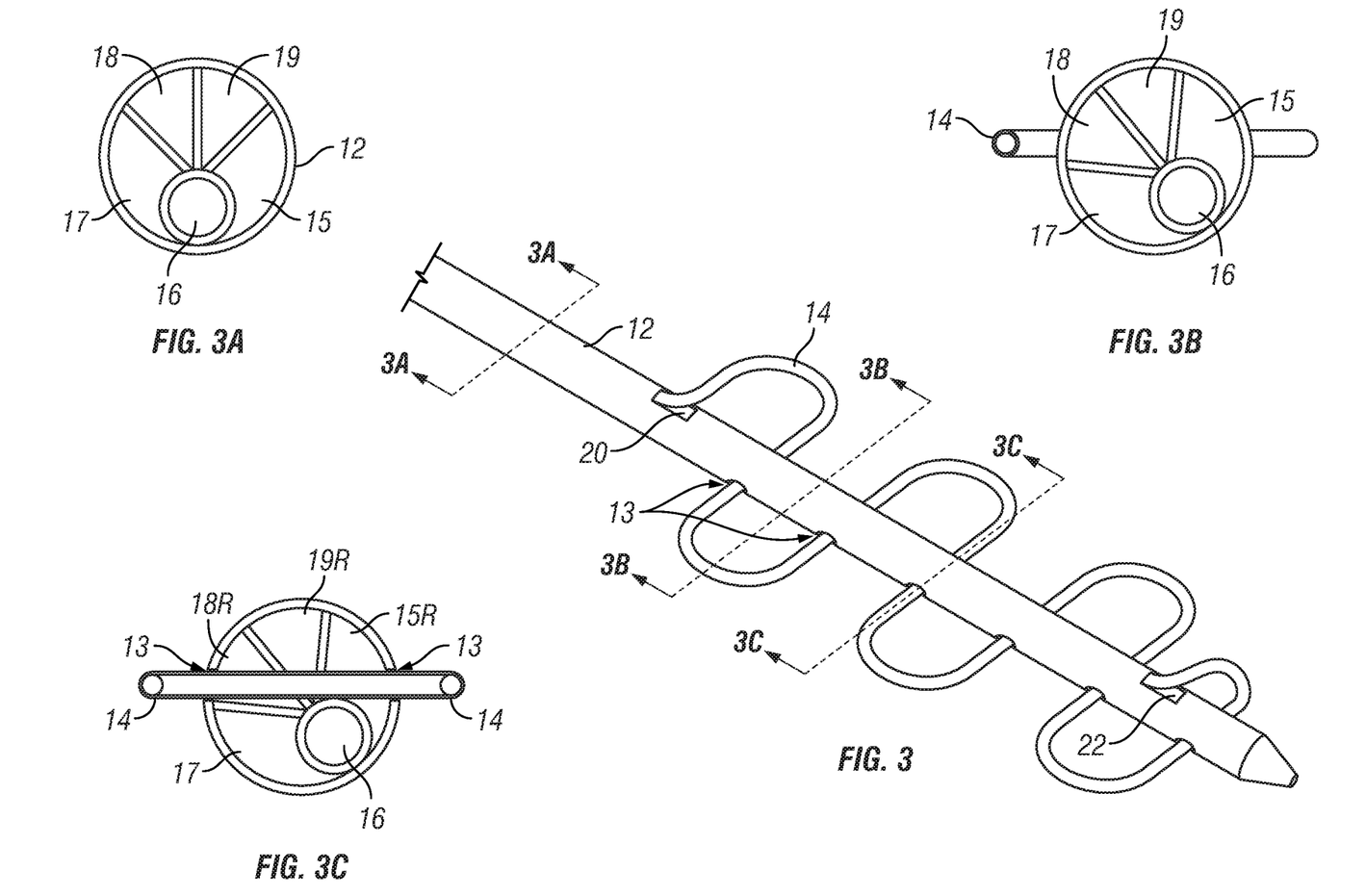
FIG. 3 is a partial perspective view of the catheter body portion of FIG. 2 having a tube passed in alternating directions through the transverse bores such that loops of the tube protrude on opposite sides of the catheter body during manufacture of a catheter device of the present invention.
FIG. 3A is a transverse cross sectional view through line 3A-3A of FIG. 3.
FIG. 3B is a transverse cross sectional view through line 3B-3B of FIG. 3.
FIG. 3C is a transverse cross sectional view through line 3C-3C of FIG. 3.

At the time of manufacture, a series of transverse bores 13 are formed through the catheter body 12, as shown in FIG. 2. These transverse bores 13 may be formed at any suitable angle relative to the longitudinal axis LA of the catheter body 12. In the particular example shown, the bores 13 are oval or ovoid shaped bores formed by advancing an oval or ovoid shaped punch through the catheter body 12 on a predetermined trajectory and such bores extend through the catheter body 12 substantially at right angles relative to the longitudinal axis LA of the catheter body 12. The trajectory of the bores 13 will avoid obliteration of any lumen(s) that are required to remain in tact to carry apparatus or thermal exchange media through that portion of the catheter body 12. In this example, optional medial infusion lumen 18 and optional proximal infusion lumen 19 are terminally sealed to proximal and medial infusion lumen outlet openings 44, 46 (seen on FIG. 4), which are located proximal to where the bores 13 are formed. Therefore, the medial and proximal infusion lumens 18, 19 are nonfunctional in the region where the bores 13 are formed. Also, in this example, the outflow lumen 15 is terminally sealed to the proximal end of tube 14 at window 20. Thus, the portion of outflow lumen 15 that extends through the region where the bores 13 are formed is non-function. Thus, in this example, the positioning of the catheter body 12 and the trajectory of the punch are controlled so that each bore 13 only obliterates unused portions of the outflow lumen 15, optional medial infusion lumen 18 and optional proximal infusion lumen 19, while leaving the inflow lumen 15 and optional distal infusion or guidewire lumen 16 in tact.

The catheter body 12 may be appropriately sized and formed of any material(s) suitable for the intended applications of the catheter device. For example, in many applications, it will be desirable for the catheter body 12 to have enough rigidity and wall thickness to contain working pressures of up to about 100 psi while being sufficiently flexible to navigate through the intended blood vessels or other body lumens to the desired location within a subject's body. Typically, this may be accomplished by a catheter body that has an outer diameter of 6 Fr (0.080") to 14 Fr (0.180") and is formed of a biocompatible polyurethane (e.g., Elastollan™ available from BASF Corporation, Florham Park, N.J. or Tecothane™ available from The Lubrizol Corporation, Wickliffe, Ohio) or polyether block amide (e.g., Pebax™ available from Arkema, Inc., Philadelphia, Pa.).

The heat exchange tube 14 may be appropriately sized and formed of any material(s) suitable for the intended applications of the catheter device. For example, in many applications, it will be desirable for the heat exchange tube 14 to a) have a thin wall thickness (typically around 0.001") to best facilitate heat transfer, b) have sufficient tensile strength to withstand pressures of up to about 100 psi and c) be sufficiently rigid or semi-rigid so as not to expand uncontrollably under pressure. Thus, it will be desirable for the tube 14 to be formed of a material capable of being extruded and/or blown into a tube having such wall thickness and properties. Examples of materials that may be suitable for forming the tube 14 include polyethylene terephthalates (PETs) available from a variety of sources or polyether block amide (e.g., Pebax™ available from Arkema, Inc., Philadelphia, Pa.).

Also, as seen in FIG. 2, a window into the inflow lumen 22 is skived or otherwise formed at a first location in a wall of the catheter body 12 and a window into the outflow lumen 20 is skived or otherwise formed at a second location in a wall of the catheter body 12. Thereafter, as illustrated FIG. 3, one end of a tube 14 is passed in alternate transverse directions (e.g., back and forth) through adjacent ones of the bores 13 so that generally U shaped loops of the tube 14 protrude outwardly from opposite sides of the catheter body. A first end (in this example the distal end) of the tube 14 is then inserted through window 22 into inflow 17 lumen and secured to the wall of the inflow lumen 17. This forms a sealed connection through which inflowing thermal exchange medium will flow from the inflow lumen 17 into the first (e.g., distal) end of the tube. Sealing attachment of the tube 14 to the luminal wall of the inflow lumen 17 may be accomplished by any suitable means such as heat sealing or by adhesive bonding. Examples of adhesives that are useable for this purpose include but are not necessarily limited to cyanoacrylate adhesives (e.g. Loctite 4011 available from the Henkel Corporate, Westlake, Ohio, UV curing acrylic adhesives (e.g., e.g. Loctite 3311 available from Henkel Corporate, Westlake, Ohio, and epoxy adhesives (e.g. Loctite 3981 available from Henkel Corporate, Westlake, Ohio). A second end of the tube 14 (in this example the proximal end) is inserted through window 20 into outflow lumen 15 and secured to the wall of the outflow lumen 15 in the same manner as described above. This forms a sealed connection through which thermal exchange medium will flow out of the tube 14 and into the outflow lumen 15. By this arrangement, thermal exchange fluid will enter the distal end of the tube 14 and will exit the proximal end of the tune 14. However, in some embodiments, it may be desirable to reverse the connections such that the proximal end of the tube 14 will be connected to the inflow lumen 17 and the distal end of the tube 14 will be connected to the outflow lumen 15. In such alternative embodiments, the trajectory of the bores 13 may obliterate the distal (unused) portion of the inflow lumen 17 while leaving that portion of the outflow lumen 15 in tact.

Figure 4:
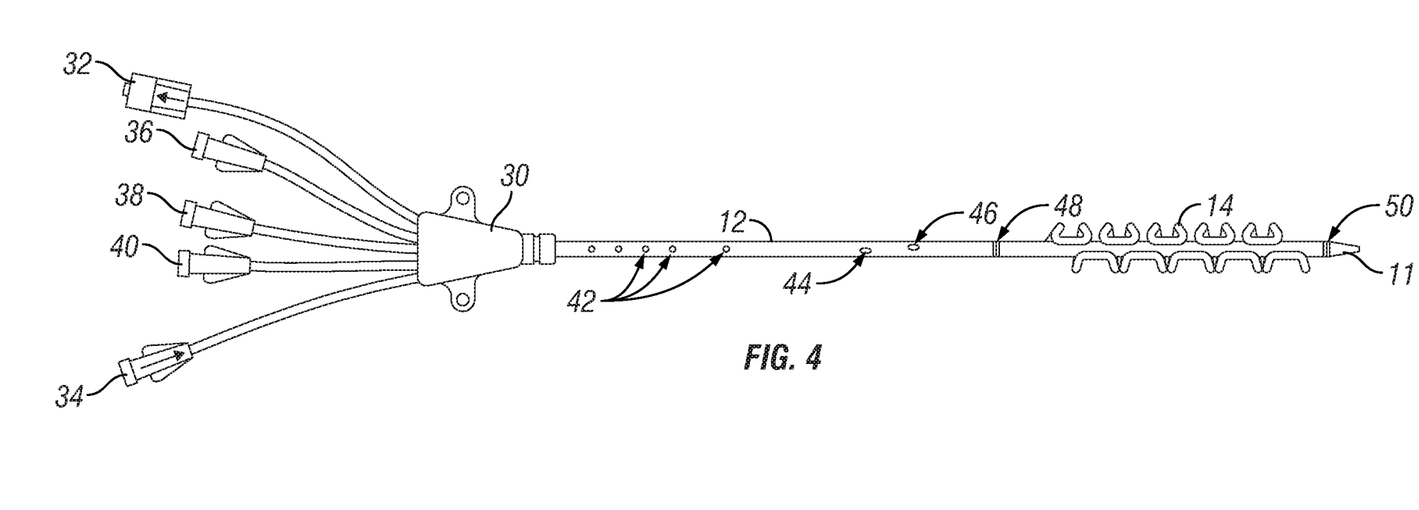
FIG. 4 is a side view of a fully assembled catheter device of the present invention.
Figure 4A:
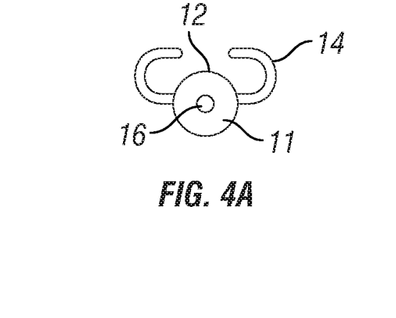
FIG. 4A is a distal end view of the catheter device of FIG. 4.

In some embodiments, it will be desirable to form the protruding U shaped loops of tubing into desired shapes by thermosetting or other suitable forming techniques. As shown in FIGS. 4 and 4A, in this example, the protruding U shaped loops of tubing 14 are formed so as to circumferentially curve around one side of the catheter body 12, as shown. Also, as shown in FIGS. 4 and 4A, when fully assembled, the catheter device of this invention includes a hub 30 on its proximal end, with an outflow lumen connector 32 (connected to outflow lumen 17), inflow lumen connector 34 (connected to inflow lumen 15), medial infusion lumen connector 36 (connected to medial infusion lumen 18), distal infusion of guidewire lumen connector 36 (connected to the distal infusion/guidewire lumen 16) and proximal infusion lumen connector 36 (connected to proximal infusion lumen 19) extending therefrom. Optional graduated distance markings 42 are formed on a proximal region of the catheter body 12 to indicate the length of catheter that is indwelling in the body at any particular time. Also, an optional proximal radiographic marker 48 and an optional distal radiographic marker 50 are located on the catheter body to facilitate radiographic determination of the location of the heat exchanging region (e.g., the protruding tube loops 14) within a subject's body.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:
1. A catheter device comprising:
an elongate body having a proximal portion and a distal portion;
the proximal portion of the elongate body having an inflow lumen and an outflow lumen;
a tube passing through a series of spaced apart locations on the distal portion such that the tube forms a series of loops that protrude outwardly from the distal portion;
the tube having a first end connected to the inflow lumen and a second end connected to the outflow lumen;

wherein transverse openings are formed at the spaced apart locations on the elongate body and the tube is positioned through those transverse openings, and wherein the transverse openings are formed at the spaced apart locations and the tube is threaded through those transverse openings.

2. A catheter device according to claim 1 further comprising a through lumen useable for at least one purpose selected from a) facilitating advancement of the catheter device over a guidewire and/or b) as a passageway for delivery of a therapeutic substance or device through the catheter device and into a subject's body.

3. A catheter device according to claim 1 wherein the loops are generally U shaped.

4. A catheter device according to claim 1, wherein the tube has a wall thickness of approximately 0.001 inch.

5. A catheter device according to claim 1 wherein the tube will withstand pressures of up to about 100 psi.

6. A catheter device according to claim 1 wherein the tube is formed of a rigid or semi-rigid material that will undergo only limited expansion in response to fluid pressure within the tube.

7. A catheter device according to claim 1 wherein the tube is formed of a polyethylene terephthalate or polyether block amide material.

8. A catheter device according to claim 1 wherein:
a window into the inflow lumen is formed at a first location and the first end of the tube extends through that window into the inflow lumen and is affixed to a wall of the inflow lumen; and
a window into the outflow lumen is formed at a second location and the second end of the tube extends through that window into the outflow lumen and is affixed to a wall of the outflow lumen.

9. A catheter device according to claim 8 wherein the window into the outflow lumen is located distal to the window into the inflow lumen such that fluid will progress through the loops in a distal direction.

10. A catheter device according to claim 8 wherein the window into the outflow lumen is located proximal to the window into the inflow lumen such that fluid will progress through the loops in a proximal direction.

11. A system comprising a catheter device according to claim 1 in combination with an apparatus for circulating heated or cooled thermal exchange fluid though the catheter device.

12. A system according to claim 11 wherein the apparatus for circulating heated or cooled thermal exchange fluid comprises a controller which controls temperature and/or flowrate of thermal exchange fluid that is circulated through the catheter device.

13. A system according to claim 12 wherein the controller receives a) an input target body temperature and b) signals from a temperature sensor indicative of a sensed body temperature and wherein the controller is programmed to vary the temperature and/or flowrate of the thermal exchange fluid in a manner that causes or attempts to cause the sensed body temperature to be the same as or within an acceptable range of the target body temperature.

14. A catheter device comprising:
an elongate body having a proximal portion and a distal portion;
the proximal portion of the elongate body having an inflow lumen and an outflow lumen;
a tube passing through a series of spaced apart locations on the distal portion such that the tube forms a series of loops that protrude outwardly from the distal portion;
the tube having a first end connected to the inflow lumen and a second end connected to the outflow lumen;
wherein a window into the inflow lumen is formed at a first location and the first end of the tube extends through that window into the inflow lumen and is affixed to a wall of the inflow lumen; and
a window into the outflow lumen is formed at a second location and the second end of the tube extends through that window into the outflow lumen and is affixed to a wall of the outflow lumen.

15. A catheter device according to claim 14 wherein the window into the outflow lumen is located distal to the window into the inflow lumen such that fluid will progress through the loops in a distal direction.

16. A catheter device according to claim 14 wherein the window into the outflow lumen is located proximal to the window into the inflow lumen such that fluid will progress through the loops in a proximal direction.

17. A catheter device comprising:
an elongate body having a proximal portion and a distal portion;
the proximal portion of the elongate body having an inflow lumen and an outflow lumen;
a tube passing through a series of spaced apart locations on the distal portion such that the tube forms a series of loops that protrude outwardly from the distal portion;
the tube having a first end connected to the inflow lumen and a second end connected to the outflow lumen;
wherein the first and second ends of the tube are secured to inflow and outflow lumens, respectively, by adhesive.

18. A system comprising:
a catheter device which comprises;
an elongate body having a proximal portion and a distal portion,
the proximal portion of the elongate body having an inflow lumen and an outflow lumen and a tube passing through a series of spaced apart locations on the distal portion such that the tube forms a series of loops that protrude outwardly from the distal portion;
the tube having a first end connected to the inflow lumen and a second end connected to the outflow lumen;
wherein transverse openings are formed at said spaced apart locations on the elongate body and the tube is positioned through those transverse openings; and
wherein transverse openings are formed at said spaced apart locations and the tube is threaded through those transverse openings in combination with:
apparatus for circulating heated or cooled thermal exchange fluid through the catheter device.

19. A system according to claim 18, wherein the apparatus for circulating heated or cooled thermal exchange fluid comprises a controller which controls temperature and/or flowrate of the thermal exchange fluid that is circulated through the catheter device.

20. A system according to claim 19 wherein the controlled receives a) an input target body temperature and b) signals from a temperature sensor indicative of a sensed body temperature and wherein the controller is programmed to vary the temperature and/or flow rate of the thermal exchange fluid in a manner that causes or attempts to cause the sensed body temperature to be the same as or within an acceptable range of the target body temperature.

21. A system according to claim 18 wherein the catheter device further comprises a through lumen useable for at least one purpose selected from a) facilitating advancement of the catheter device over a guidewire and/or b) as a passageway for delivery of a therapeutic substance or device through the catheter device and into a subject's body.

22. A system according to claim 18 wherein the loops are generally U shaped.

23. A system according to claim 18 wherein the tube has a wall thickness of approximately 0.001 inch.

24. A system 1 according to claim 18 wherein the tube will withstand pressures of up to about 100 psi.

25. A system according to claim 18 wherein the tube is formed of a rigid or semi-rigid material that will undergo only limited expansion in response to fluid pressure within the tube.

26. A system according to claim 18 wherein the tube is formed of a polyethylene terephthalate or polyether block amide material.

* * * * *

UNITED STATES PATENT AND TRADEMARK OFFICE
CERTIFICATE OF CORRECTION

PATENT NO. : 10,869,989 B2
APPLICATION NO. : 15/350918
DATED : December 22, 2020
INVENTOR(S) : Jeremy Thomas Dabrowiak

Page 1 of 1

It is certified that error appears in the above-identified patent and that said Letters Patent is hereby corrected as shown below:

In the Claims

Column 9, Line 9, Claim 24, after "system", delete "1"

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*